United States Patent [19]

Brougham et al.

[11] Patent Number: 5,545,343
[45] Date of Patent: Aug. 13, 1996

[54] PERACID COMPOSITIONS FOR MEDICAL DISINFECTION

[75] Inventors: Paul Brougham, Rainhill; Robert A. Simms, Woolston, both of United Kingdom

[73] Assignee: Solvay Interox Limited, Warrington, United Kingdom

[21] Appl. No.: 211,659

[22] PCT Filed: Oct. 8, 1992

[86] PCT No.: PCT/GB92/01830

§ 371 Date: Jun. 21, 1994

§ 102(e) Date: Jun. 21, 1994

[87] PCT Pub. No.: WO93/07909

PCT Pub. Date: Apr. 29, 1993

[30] Foreign Application Priority Data

Oct. 17, 1991 [GB] United Kingdom ............... 9122048

[51] Int. Cl.$^6$ ........................................... A01N 59/00
[52] U.S. Cl. .................. 514/557; 252/387; 252/389.2; 252/186.26; 422/28; 510/372
[58] Field of Search ............................ 422/28, 32, 37; 562/3, 4, 6; 252/142, 95, 97, 173, 387, 389.2, 357

[56] References Cited

U.S. PATENT DOCUMENTS

| | | | |
|---|---|---|---|
| 3,759,594 | 9/1973 | Cobb | 312/31 |
| 4,150,024 | 4/1979 | Syldatk et al. | 252/357 |
| 4,276,263 | 6/1981 | Andersen et al. | 422/37 |
| 4,297,298 | 10/1981 | Crommelynck et al. | 562/3 |
| 4,557,898 | 12/1985 | Greene et al. | 422/28 |
| 5,037,623 | 8/1991 | Schneider et al. | 422/292 |
| 5,077,008 | 12/1991 | Kralovic et al. | 422/37 |
| 5,130,053 | 7/1992 | Feasey et al. | 252/400.22 |

FOREIGN PATENT DOCUMENTS

| | | |
|---|---|---|
| 0354186 | 2/1990 | European Pat. Off. . |
| 0426949 | 5/1991 | European Pat. Off. . |
| 0551904 | 7/1975 | Germany . |

OTHER PUBLICATIONS

Chemical Abstracts, 93:52264d (1980), vol. 93. p. 353.
Chemical Abstracts, 104:167038w (1986), vol. 104, p. 547.
Chemical Abstracts, 83:64532w (1975), vol. 83, p. 385.

*Primary Examiner*—Robert J. Warden
*Assistant Examiner*—Hien Tran
*Attorney, Agent, or Firm*—Larson and Taylor

[57] ABSTRACT

A multi-component product for providing, on mixing of the components, a disinfectant composition. A first component of the product comprises an aqueous solution of a lower aliphatic peracid and a second component comprises an aqueous solution containing a corrosion inhibitor and either a hydrogen peroxide stabilizer, a peracid stabilizer, or both.

30 Claims, No Drawings

PERACID COMPOSITIONS FOR MEDICAL DISINFECTION

This invention concerns compositions, processes for the preparation of such compositions, two-pack systems for preparing such compositions and uses of such compositions. More particularly the present invention concerns compositions comprising dilute aqueous solutions of lower aliphatic peracids and their use as disinfectant compositions.

The lower aliphatic peracids are effective wide-spectrum bactericides which have the particular advantage, in use, of leaving as residues only the corresponding lower aliphatic acids and therefore being particularly suitable for applications which require a non-environmentally-polluting disinfectant. While the lower aliphatic peracids in general are contemplated herein, for example those corresponding to carboxylic aliphatic acids containing 2 to 9 carbon atoms, peracetic acid is particularly envisaged since it is already a commercially important peracid for disinfectant purposes. Where the following description relates to peracetic acid it is to be understood that the other peracids may be read in substitution therefor provided that the technical context allows it.

Aqueous solutions of peracetic acid containing up to about 45 % by weight of peracetic acid are commercially available. Such solutions may be produced by reacting appropriately concentrated hydrogen peroxide and acetic acid in an aqueous medium in the presence of an acid catalyst which is usually sulphuric acid or other strong mineral acid. The acid catalyst may be present in from about 0.1% to about 5% by weight of the reaction mixture.

Aqueous solutions of peracetic acid represent equilibrium mixtures of the reactants and the reaction products and, under relatively forcing reaction conditions, for example when using one or more of a substantial quantity of catalyst, an elevated reaction Temperature and a concentrated reaction mixture, equilibrium may be substantially reached in a relatively short time. When using the strong acid catalyst in from 2% to 5% of the reaction mixture, a temperature of from 30° C. to 50° C. and a concentration of acid above about 20% by weight the reaction mixture may come to equilibrium within hours. For some applications, or where long storage is envisaged, it may not be desirable for there to be catalyst residues in a peracid product particularly, for example, dilute products intended for personal or domestic hygiene use. For many applications dilute solutions of peracetic acid, for example below 5% by weight but often below 2%, for example from 0.1% to 2% by weight, are required. Concentrations of peracetic acid above 0.5% by weight for example from 0.5% to 1% by weight, are particularly effective bactericidally in, for example, toilet cleansing applications. Such dilute peracetic acid solutions may be produced directly by reacting acetic acid and hydrogen peroxide in a suitably dilute reaction medium but equilibrium can take an extremely long time to reach, particularly at the more extreme dilutions envisaged. At peracid concentrations below 1% by weight equilibrium may take a month or more to reach if the reaction is not acid catalyzed or a week or more even if the reaction is acid catalyzed. This entails a very heavy utilization of plant and equipment on a large production scale.

If a concentrated equilibrium solution of peracetic acid is diluted with water the equilibrium point of the system is progressively altered, as dilution progresses, in favour of the regeneration of the original reactants. The ageing time taken to attain the new equilibrium point, after dilution, is of a similar order to that required to produce such a dilute solution directly from suitable reactants. Such a diluted solution may be used directly although it is not at equilibrium and is therefore of variable composition in storage. Such non-equilibrium diluted solutions also have a composition dictated by the equilibrium point applying at the original concentration, which may not be desired in some applications. In 1955 Greenspan et al.( Proc. 42nd Ann. Mtg. Chem. Spec. Man. Ass. Dec. 1955), disclosed that stable dilute peracetic acid solutions can be prepared by the use of peracid stabilizers in conjunction with proper adjustment of the relative concentrations of the components of the dilute peracid solution, that is to say that, if the prepared dilute solution is not fully at equilibrium, adjustment of the balance of the components can achieve stability. The solutions in question may be prepared by dilution of commercial, e.g. fully equilibrated peracetic acid which has been produced by the use of small amounts of a mineral acid catalyst.

U.S. Pat. No. 4,297,298 describes the production of an aqueous solution of a lower aliphatic peracid by preparing in a first process step a concentrated solution of the peracid from the corresponding carboxylic acid or anhydride and concentrated hydrogen peroxide in the presence of a small quantity of a strong acid catalyst and diluting the solution with a solution containing at least one of the reagents from the first process step so as to bring the concentration of the aliphatic peracid to the rated concentration of the mixture the concentration of the diluent reagent or reagents being chosen "so that once dilution has been brought about, the system is no longer at equilibrium, but tends to move in the direction of forming further aliphatic peracid at a very slow rate." The process specifically described in U.S. Pat. No. 4,297,298 produces a non-equilibrium composition which contains an extremely high concentration of hydrogen peroxide, e.g. from 28% to 46%. Such a concentration on contact with the user would cause skin bleaching and pain.

U.S. Pat. No. 4,743,447 describes the production of solutions having a hydrogen peroxide base for disinfecting contact lenses, the solution having from 0.005% to 0.1% by weight of peracetic acid, 1% to 8% by weight of hydrogen peroxide and sufficient acetic acid for the system to reach equilibrium. Such a solution may be prepared by direct reaction using a very dilute reaction mixture with lengthy equilibration or from a stable commercial solution having a "weak concentration" of peracetic acid to which the other constituents of the composition are added. This teaching does not therefore avoid the separate initial step of producing a stable weak solution of peracetic acid from which to produce in turn the final product.

EP-A-0357238 (Steris Corp) discloses an anti-microbial composition comprising a strong oxidant, a copper and brass corrosion inhibitor, a buffering agent, at least one anti-corrosive agent which exhibits corrosion inhibition in at least aluminium, carbon steel and stainless steel, and a wetting agent. The corrosion inhibitors specifically disclosed for brass and aluminium comprise triazoles and molybdates, which are known to have unfavourable toxicity, and which therefore renders undesirable their use in a medical environment.

It is an object of the present invention to provide a disinfectant composition, based on a dilute solution of peracid, which may be used on medical equipment comprising metal components to be disinfected.

In accordance with the present invention there is provided a process for the preparation of an aqueous disinfectant composition characterized in that the process comprises mixing a first aqueous solution comprising a lower aliphatic peracid with a second aqueous solution comprising a corrosion inhibitor and a hydrogen peroxide stabilizer and/or peracid stabilizer.

In another aspect, the present invention provides a disinfectant composition obtainable by a process comprising mixing a first aqueous solution comprising a lower aliphatic peracid with a second aqueous solution comprising a corrosion inhibitor and a hydrogen peroxide stabilizer and/or peracid stabilizer. It is to be understood that the peracid composition of the present invention is not in equilibrium and comprises a relatively higher concentration of stabilizer(s) than a skilled person would expect to find in a composition which is in equilibrium and comprises a similar concentration of peracid In yet another aspect, the present invention provides a two-pack system for the preparation of a disinfectant composition, characterised in that one pack comprises a first aqueous solution comprising a lower aliphatic peracid, and the other pack comprises a second aqueous solution comprising a corrosion inhibitor and a hydrogen peroxide stabilizer and/or peracid stabilizer.

The first aqueous solution preferably comprises a lower aliphatic peracid, such as peracetic acid, in an amount of from 2% to 10%, more preferably from 3% to 7%, by weight of the solution. The first aqueous solution may additionally comprise stabilizer(s) for the hydrogen peroxide and/or the peracid in the equilibrium solution, each relevant stabilizer being present in a preferred amount of from 20 to 10,000 ppm. Preferably both the peroxide and peracid are stabilized in the solution, giving a preferred combined stabilizer concentration of from 3000 to 6000 ppm. A suitable peracid stabilizer is dipicolinic acid and suitable peroxide stabilizers include phosphonic acids and salts thereof, e.g. the products sold by Monsanto under the trade mark "DEQUEST" such as hydroxyethylidenediphosphonate, diethylenetriaminepentamethylene phosphonate and ethylenediaminetetramethylene phosphonate and those stabilizers claimed in European patent application 0426949, especially cyclohexane-1, 2-diaminotetramethylenephosphonic acid and salts thereof (CDTMP). It should be understood that the first solution is usually an equilibrium mixture of the relevant reactants and reaction products, as generally described in the paragraph bridging page 1 and page 2 above, and that the above specified amount of peracid indicates the amount of peracid per se in the solution. A preferred process for the preparation of dilute solutions of lower aliphatic peracids useful in the present invention is disclosed in PCT Patent Application No. WO 91/13058.

The second aqueous solution preferably comprises from 0.1% to 5%, more preferably from 0.1% to 1%, by weight of the solution of a corrosion inhibitor. Preferably, the corrosion inhibitor is an alkali metal phosphate, most preferably a potassium phosphate. Dipotassium hydrogen orthophosphate ($K_2HPO_4$) is the most preferred corrosion inhibitor.

The second aqueous solution preferably comprises from 0.1% to 2%, often 0.1% to 1%, more preferably from 0.2% to 0.7% or 0.7% to 1%, by weight of the solution of hydrogen peroxide stabilizer and/or peracid stabilizer, such as about 0.5% or about 1% stabilizer. Preferably a hydrogen peroxide stabilizer is used, The preferred peroxide stabilizers are phosphonic acids and salts thereof, for example, those described hereinabove as suitable for the first aqueous solution. A suitable peracid stabilizer is dipicolinic acid.

Mixing of the first and second solutions give a disinfectant composition immediately after mixing comprising at least 0.05% and generally not greater than 1% by weight peracid. In many embodiments, the mixture of the two solutions immediately after mixing comprises from 0.1% to 0.25% or from 0.25% to 0.5% by weight peracid. The mixture also desirably comprises from 0.1% to 5% corrosion inhibitor and from 0.1% to 1% peroxide stabilizer and/or peracid stabilizer. Such mixtures can often be obtained conveniently by selecting a volume ratio of the first solution to the second solution which is often at least 1:5 and not usually greater than 1:50, preferably from 1:10 to 1:30, taking into account the concentration of the components in each solution.

One or both of the aqueous solutions may contain other components useful in disinfectant compositions, e.g. a triazole corrosion inhibitor and/or a wetting agent, though the presence of these components is not essential to obtain the advantages of the invention (indeed, such components may be slightly detrimental). One or both of the solutions may contain an indicator which undergoes a colour change to indicate that the two solutions have been mixed together.

It will be appreciated that the compositions provided by the process of the present invention are not in equilibrium and that in the natural course of events the peracid component of the composition will tend towards equilibrium. For example, the composition described in the paragraph immediately above this paragraph will begin to change within a relatively short period of time from mixing the first and second solutions together and that as time passes the peracid concentration in the solution will reduce as it tends towards equilibrium. Normal equilibrium could be expected to be reached after about two days, assuming the peracid and/or peroxide does not decompose in that period.

The compositions of the present invention are particularly suitable for use as medical disinfectants. Preferably, the compositions are used to disinfect medical equipment which has metal, e.g. aluminium, brass, copper and especially steel, components required to be disinfected. For example, the composition is particularly useful for disinfection of endoscopes. The present invention may have a further advantage over the prior art compositions of Steris. The selected components of the invention composition interact to protect metal components, especially steel components, with regard to localized corrosion, e.g. pitting, as well as, if not better than, if molybdate, triazole and/or wetting agent were present. This is most surprising in light of the disclosure on page 4, lines 7 to 9, of Steris.

The present invention has the advantage of providing a dilute composition comprising a relatively high concentration of peracid. Furthermore, the process of the present invention enables a relatively longer shelf life for the separate aqueous solution than would be achieved if the composition was supplied per se.

The invention will now be further described, without limitation, with reference to the following examples:

EXAMPLE 1

Preparation of Composition according to the Present Invention

A two-pack system was prepared. One pack contained 250 ml of an aqueous peracetic acid, 5% (active) by weight, solution. The other pack contained 10 l of an aqueous solution comprising 0.6% by weight dipotassium hydrogen ortho phosphate and 0.5% by weight CDTMP. The two packs were then mixed together to form a composition of the present invention.

EXAMPLE 2

Preparation of Composition according to the Present Invention

A solution of 5% w/w peracetic acid, 20% w/w hydrogen peroxide, 8% w/w acetic acid was diluted 14 times with a solution containing 1% w/w CDTMP and 0.8% dipotassium hydrogen orthophosphate to form a solution containing 3,500 ppm peracetic acid.

EXAMPLE 3 AND COMPARISON A

Corrosion Trials for Disinfectant Compositions

Duplicate coupons of mild steel and stainless steel 316 were immersed for 72 hours at room temperature (15°–25° C.) in disinfectant solutions. In Example 3, the disinfectant solution was prepared according to the method of Example 2 after a dilution by 25 times to produce a solution containing 2000 ppm peracetic acid. In Comparison A, the disinfectant solution was prepared according to the example given in the first table, page 6, lines 1 to 18 of European Patent Application No 0 357 238. The solutions were completely replaced daily with fresh solutions. Examination of the coupons with both the naked eye and an optical microscope on completion of the trial showed that for both of the metals in the composition according to the Steris Application, there was significant localized corrosion and pitting on the metal but for the metals in the disinfectant solution according to the present invention there was only very slight localised corrosion.

The significant reduction in localized corrosion achieved with compositions according to the present invention is surprising given the disclosure on page 4, lines 7 to 9 of the Steris Application, and is particularly advantageous because the results were achieved without the use of any toxic molybdate and triazole.

We claim:

1. A process for the preparation of an aqueous disinfectant composition comprising mixing a first aqueous solution comprising a lower aliphatic peracid with a second aqueous solution comprising a phosphate corrosion inhibitor and at least one hydrogen peroxide stabilizer selected from the group consisting of phosphonic acids and salts thereof.

2. A process as claimed in claim 1, wherein the first aqueous solution comprises a ($C_2$–$C_9$) aliphatic peracid in an amount of from 2% to 10% by weight of the first aqueous solution.

3. A process as claimed in claim 1, wherein the first aqueous solution comprises a ($C_2$–$C_9$) aliphatic peracid in an amount of from 3% to 7% by weight of the first aqueous solution.

4. A process as claimed in claim 2 or 3, wherein the aliphatic peracid comprises peracetic acid.

5. A process as claimed in claim 1, 2 or 3 wherein the second aqueous solution comprises from 0.1% to 5% by weight of the second aqueous solution of the phosphate corrosion inhibitor.

6. A process as claimed in claim 5, wherein the second aqueous solution comprises from 0.1% to 1% by weight of the second aqueous solution of the phosphate corrosion inhibitor.

7. A process as claimed in claim 5, wherein the phosphate corrosion inhibitor comprises an alkali metal phosphate.

8. A process as claimed in claim 6 wherein the phosphate corrosion inhibitor comprises dipotassium hydrogen orthophosphate.

9. A process as claimed in claim 1 wherein the second aqueous solution comprises from 0.1% to 2% by weight of the second aqueous solution of said at least one hydrogen peroxide stabilizer.

10. A process as claimed in claim 9 wherein the second aqueous solution comprises from 0.2% to 1% by weight of the second aqueous solution of said at least one hydrogen peroxide stabilizer.

11. A process as claimed in claim 1 wherein said hydrogen peroxide stabilizer comprises cyclohexane-1, 2-diaminotetramethylenephosphonic acid or salt thereof.

12. A process as claimed in claim 1, 2, 3, 9 or 10, wherein the ratio of the volume of the first aqueous solution to the volume of the second aqueous solution is 1:5 to 1:50.

13. A process as claimed in claim 12 wherein the ratio of the volume of the first aqueous solution to the volume of the second aqueous solution is 1:10 to 1:30.

14. A process as claimed in claim 1, 2, 3, 9 or 10, wherein at least one of the first and second aqueous solutions comprises an indicator which undergoes a colour change when the solutions are mixed together.

15. A process according to any one of claims 1, 2, 3, 9 or 10, wherein said phosphate corrosion inhibitor comprises a steel corrosion inhibitor.

16. A multi-component product for providing, on mixing of the components, a disinfectant composition, said product comprising a first component which comprises a first aqueous solution comprising a lower aliphatic peracid, and a second component which comprises a second aqueous solution comprising a phosphate corrosion inhibitor and at least one hydrogen peroxide stabilizer selected from the group consisting of phosphonic acids and salts thereof.

17. A multi-component product as claimed in claim 16, wherein the first aqueous solution comprises a ($C_2$–$C_9$) aliphatic peracid in an amount of from 2% to 10% by weight of the first aqueous solution.

18. A multi-component product as claimed in claim 16, wherein the first aqueous solution comprises a ($C_2$–$C_9$) aliphatic peracid in an amount of from 3% to 7% by weight of the first aqueous solution.

19. A multi-component product as claimed in claim 17 or 18, wherein the aliphatic peracid comprises peracetic acid.

20. A multi-component product as claimed in claim 16, 17 or 18 wherein the second aqueous solution comprises from 0.1% to 5% by weight of the second aqueous solution of the phosphate corrosion inhibitor.

21. A multi-component product as claimed in claim 20, wherein the second aqueous solution comprises from 0.1% to 1% by weight of the second aqueous solution of the phosphate corrosion inhibitor.

22. A multi-component product as claimed in claim 20, wherein the phosphate corrosion inhibitor comprises an alkali metal phosphate.

23. A multi-component product as claimed in claim 21 wherein the phosphate corrosion inhibitor comprises dipotassium hydrogen orthophosphate.

24. A multi-component product as claimed in claim 16 wherein the second aqueous solution comprises from 0.1% to 2% by weight of the second aqueous solution of said at least one hydrogen peroxide stabilizer.

25. A multi-component product as claimed in claim 28 wherein the second aqueous solution comprises from 0.2% to 1% by weight of the second aqueous solution of said at least one hydrogen peroxide stabilizer.

26. A multi-component product as claimed in claim 16 wherein said hydrogen peroxide stabilizer comprises cyclohexane-1, 2-diaminotetramethylenephosphonic acid or salt thereof.

27. A multi-component product as claimed in claim 16, 17, 18, 24 or 25, wherein the ratio of the volume of the first aqueous solution to the volume of the second aqueous solution is 1:5 to 1:50.

28. A multi-component product as claimed in claim 27 wherein the ratio of the volume of the first aqueous solution to the volume of the second aqueous solution is 1:10 to 1:30.

29. A multi-component product as claimed in claim 16, 17, 18, 24 or 25, wherein at least one of the first and second aqueous solutions comprises an indicator which undergoes a colour change when the solutions are mixed together.

30. A multi-component product according to any one of claims 16, 17, 18, 24 or 25, wherein said phosphate corrosion inhibitor comprises a steel corrosion inhibitor.

* * * * *